United States Patent
Vasic et al.

(10) Patent No.: US 7,030,371 B2
(45) Date of Patent: Apr. 18, 2006

(54) LUMINESCENCE CHARACTERISTICS DETECTOR

(75) Inventors: Milan Vasic, Geneva (CH); Edgar Muller, Fribourg (CH); Myron Seto, Lausanne (CH)

(73) Assignee: SICPA Holding S.A., Prilly (CH)

( * ) Notice: Subject to any disclaimer, the term of this patent is extended or adjusted under 35 U.S.C. 154(b) by 0 days.

(21) Appl. No.: 10/240,737

(22) PCT Filed: Jan. 26, 2002

(86) PCT No.: PCT/EP02/00811

§ 371 (c)(1), (2), (4) Date: Nov. 8, 2002

(87) PCT Pub. No.: WO02/071347

PCT Pub. Date: Sep. 12, 2002

(65) Prior Publication Data

US 2004/0061048 A1 Apr. 1, 2004

(51) Int. Cl.
*G01N 21/64* (2006.01)
*G06K 7/10* (2006.01)

(52) U.S. Cl. ............. 250/271; 250/458.1; 250/459.1

(58) Field of Classification Search ............. 250/271, 250/458.1, 459.1, 461.1, 461.2
See application file for complete search history.

(56) References Cited

U.S. PATENT DOCUMENTS

| | | | |
|---|---|---|---|
| 3,656,835 A | 4/1972 | Johnson et al. | |
| 4,275,299 A | 6/1981 | Favre | |
| 4,438,329 A * | 3/1984 | Ford et al. ............ | 250/459.1 |
| 5,043,585 A | 8/1991 | Fehrenbach et al. | |
| 5,315,993 A | 5/1994 | Alcala | |
| 5,331,140 A | 7/1994 | Stephany | |
| 5,418,855 A | 5/1995 | Liang et al. | |
| 5,548,106 A | 8/1996 | Liang et al. | |
| 5,548,124 A | 8/1996 | Takeshima et al. | |
| 5,574,790 A | 11/1996 | Liang et al. | |
| 5,608,225 A | 3/1997 | Kamimura et al. | |
| 5,757,013 A | 5/1998 | Groger et al. | |
| 5,918,960 A | 7/1999 | Hopwood et al. | |
| 6,303,929 B1 * | 10/2001 | Oshima et al. ......... | 250/271 |

FOREIGN PATENT DOCUMENTS

EP 0760944 4/2002

* cited by examiner

Primary Examiner—Constantine Hannaher
(74) Attorney, Agent, or Firm—Shoemaker and Mattare

(57) ABSTRACT

Security documents or articles carrying luminescent marker compounds which show a time-deferred emission characteristic are authenticated by a method and device which allows for rapid extraction of characteristic luminescent parameters, such as emission intensity and time constants. The method is not sensitive to perturbations by ambient light and reduces optical filtering requirements.

28 Claims, 5 Drawing Sheets

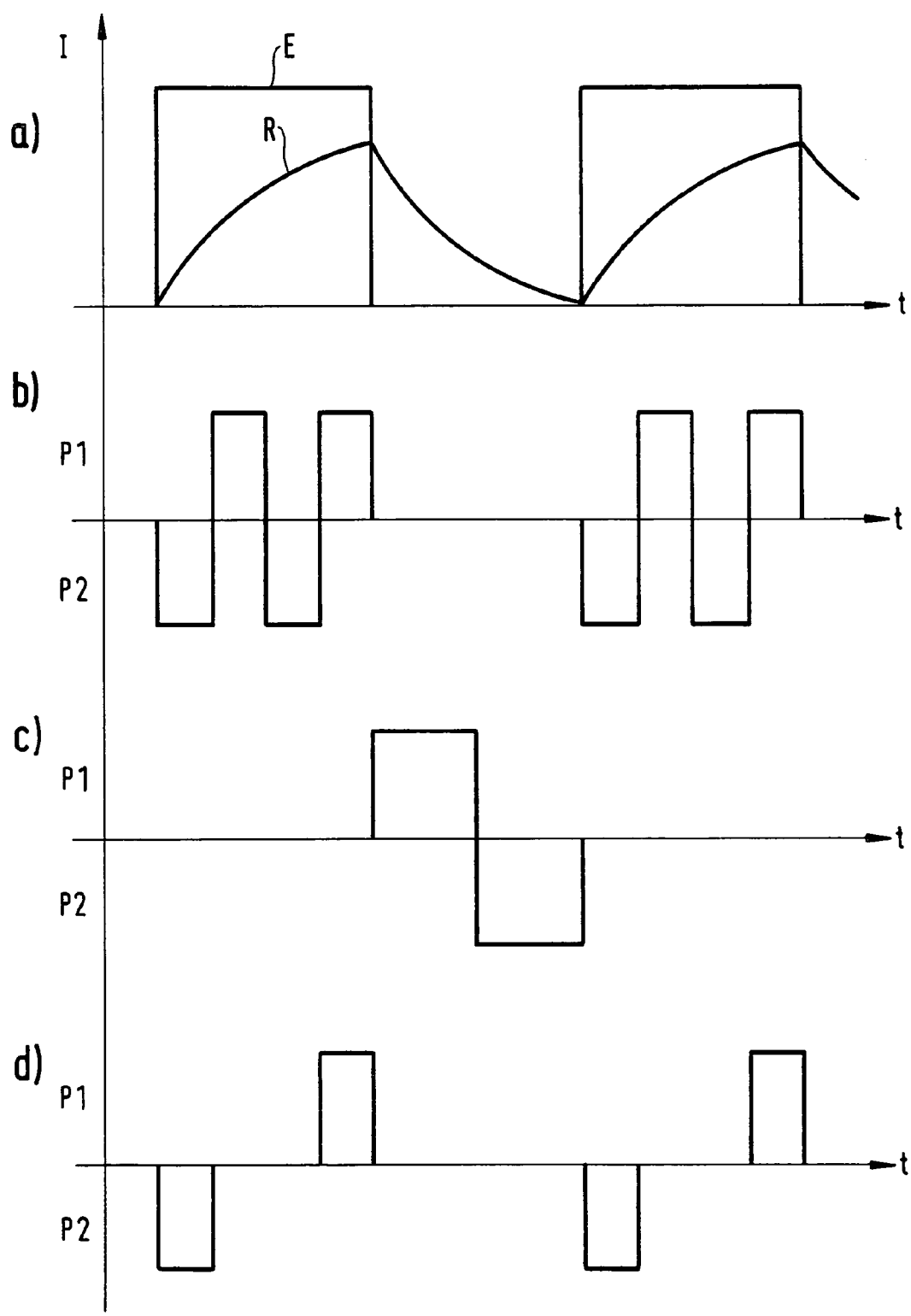

LUMINESCENCE CHARACTERISTICS DETECTOR

FIELD OF INVENTION

Figure 1:
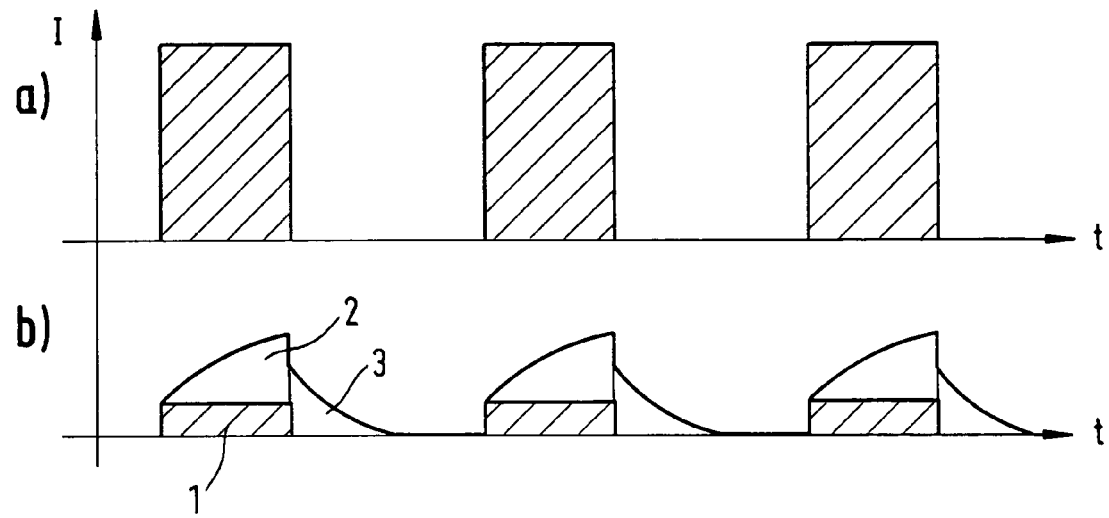

The invention is in the field of security documents and articles. It concerns a method of determining the authenticity of such documents or articles. In particular, it concerns security documents or articles carrying a luminescent feature, and a device for the quantitative measurement of the luminescence emission intensity and characteristics of said luminescent feature.

BACKGROUND OF THE INVENTION

Luminescent compounds are well known security elements for the protection of banknotes, valued papers and other security articles. Such compounds may be incorporated into the security article's substrate, printed onto security articles via an ink, or affixed to security articles in the form of a security thread, a foil or a label carrying them.

The detection of luminescent security elements is well known in the art and described in a large number of patents. U.S. Pat. No. 5,918,960 describes a counterfeit banknote detecting apparatus, based on a UV lamp to excite the luminescence, and two photocells, to measure the luminescence intensity versus the background radiation intensity. A particular problem in luminescence detection is the discrimination of the weak luminescence signal from the often much stronger background signals, which are due to environmental light. The use of modulated excitation and synchronous detection has been proposed as a possibility to overcome this difficulty.

U.S. Pat. No. 5,608,225 describes an improved fluorescent detecting apparatus and a method using a modulated excitation source, a photocell, and a phase detector, for the suppression of background signals. U.S. Pat. Nos. 4,275,299, 5,548,106, 5,418,855 and 5,574,790 describe further detection equipment based on modulated excitation. U.S. Pat. No. 3,656,835 teaches the joint use of a constant UV-excitation source and a modulated magnetic field, to produce and detect modulated emission from magnetic triplet states of the luminescent. U.S. Pat. Nos. 5,315,993 and 5,331,140 propose luminescence decay monitoring using a multiplexing of more than one modulation frequency of the excitation source, e.g. for the reading of invisible fluorescent barcodes. U.S. Pat. Nos. 5,548,124 and 5,757,013 propose the measurement of luminescence decay times through the generation of a modulation product of the excitation signal and the back-received luminescent response signal.

The modulation-based luminescence detection systems of the prior art are quite rugged against environment light influences which do not have the same modulation frequency and phase as the detector's own light source. They are, on the other hand, very sensitive to their own modulation frequency. Some of the modulated excitation light is noteworthy back-scattered at the sample surface and leaks through the optical filter system into the detector's photocell. No optical filter system has noteworthy a 100% rejection of the off-band light components. This residual excitation light, which has exactly the same frequency as the luminescence response, adds thus to the detected signal intensity. In the case of a weak luminescence signal, said background signal impedes a proper determination of the luminescence signal intensity.

This is the more disturbing as the background signal depends on the reflectivity of the substrate, which may vary independently of the luminescence signal intensity. In the case of banknote authentication, the substrate reflectivity depends noteworthy on external factors such as dirtiness and wear, which makes it difficult to check the banknote fore genuineness if no distinction can be made between the merely reflected background signal and the true luminescence emission signal.

The present invention discloses a method and an equipment which overcome the shortcomings of the prior art.

In particular it discloses a method and an equipment which allow to discriminate between the reflected excitation signal and the luminescence emission signal, and to determine selectively the strength of the luminescence emission.

The present invention allows furthermore for a quantitative determination of luminescence intensity, independent of background reflectivity.

It allows further to derive absolute or comparative luminescence intensities, and to exploit these for coding and identification purposes.

SUMMARY OF THE INVENTION

The present invention discloses a method which allows for the determination of luminescence intensities, free of contributions from ambient light and from back-scattered excitation radiation. It relies on the use of at least one luminescent compound showing a time-deferred emission characteristics, i.e. having a time-dependent build-up of the luminescence emission after the excitation light source has been switched on, and still emitting a decaying luminescence signal after the excitation light source has been switched off. A typical emission response of such a luminescent as a function of time is shown in FIG. 1: a) shows the intensity versus time of a pulsed excitation radiation of wavelength $\lambda 1$; b) shows the intensity versus time of the detected response from the luminescent. Said detected response comprises at least three components: (1) back-scattered radiation of wavelength $\lambda 1$ leaking through the optical filter system, (2) luminescence radiation of wavelength $\lambda 2$ emitted during excitation, and (3) luminescence radiation of wavelength $\lambda 2$ emitted after excitation.

The existence of back-scattered radiation (1) at the detector makes it difficult to obtain accurate absolute measurements for the real emitted luminescence intensity, such as reflected by its "rise part" (2) and its "decay part" (3). This is particularly true in the case of weak luminescence and high excitation intensity, e.g. in the case where an up-converting phosphor must be detected.

Figure 2:
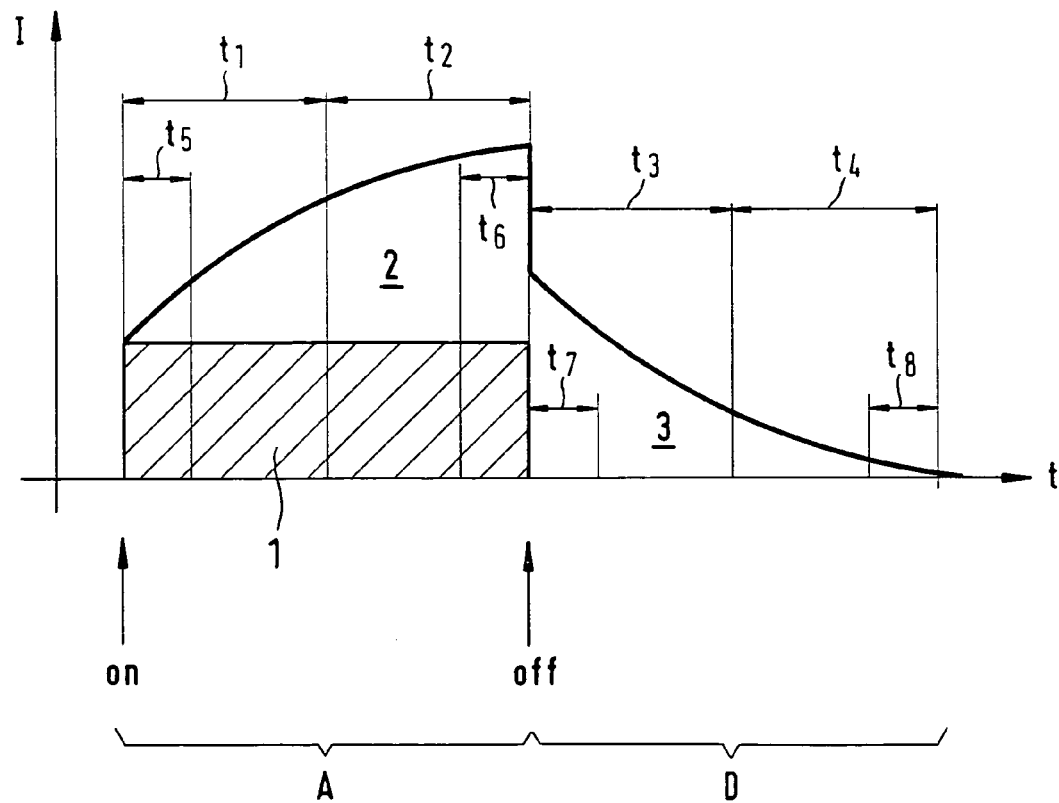

The method according to the present invention, which overcomes this problem, is examplified in connection with FIG. 2. The excitation light source is periodically switched on and off, as shown in FIG. 1. A measured value for the net luminescence intensity can be obtained for both, the "rise" and the "decay" parts by using the following method:

The "rise" interval (A) between the switching-on and the switching-off of the excitation light source may be subdivided into at least two time intervals which are preferably equal. The detector signal is integrated during said time intervals to achieve values for each interval. Then the difference between the first and the second signal is calculated. Due to the fact that the time intervals are equal, the leakage contribution (1) of back-scattered excitation radiation is subtracted out, together with the otherwise present background radiation (ambient light). The remaining signal intensity is exclusively due to the luminescence emission.

In the example of FIG. 2, the "rise interval" (A) may, for example, be entirely subdivided into two equal time intervals (t1, t2). The integrated signal intensity during time interval t1 is subtracted from the integrated signal intensity during time interval t2. Contributions from back-scattering, background radiation and other light influences causing an error are collectively called back-scattering contributions 1. By subtracting intensity values a net signal value is achieved which is representative of the luminescence intensity only.

Alternatively, the "rise interval" (A) may be partially subdivided into two equal time intervals (t5, t6), said time intervals being shorter than the former time intervals (t1, t2) and located near the beginning and near the end of the "rise interval" (A) . Preferably, at least one of the intervals t5, t6 is shorter than 25% of the rise interval "A" during which the compound is exposed to the excitation light source. The integrated signal intensity during time interval t5 is subtracted from the integrated signal intensity during time interval t6. Contributions from back-scattering (1) and background radiation cancel out, to leave a net signal value, representative of the luminescence intensity only. This alternative solution is particularly suitable if several luminescent materials, having very different characteristic "rise" time constants, must be analyzed using one and the same detection equipment.

Similarly, the "decay" interval (D) following the switching-off of the excitation light source may be subdivided into at least two, preferably equal time intervals. The detector signal is integrated during said time intervals, and at least one difference signal between a later and an earlier, equal, time interval is formed. Due to the fact that the time intervals are equal, the otherwise present background radiation (ambient light) is subtracted out. The remaining signal is exclusively due to the presence of the luminescence emission.

In the example of FIG. 2, the "decay interval" (D) may be entirely subdivided into two equal time intervals (t3, t4). The integrated signal intensity during time interval t3 is subtracted from the integrated signal intensity during time interval t4. Contributions from background radiation cancel out, to leave a net signal value, representative of the sole luminescence intensity.

Alternatively, the "decay interval" (D) may be partially subdivided into two equal time intervals (t7, t8), said time intervals being shorter than the former time intervals (t3, t4) and located near the beginning and near the end of the "decay interval" (D). The integrated signal intensity during time interval t7 is subtracted from the integrated signal intensity during time interval t8. Contributions from background radiation cancel out, to leave a net signal value, representative of the sole luminescence intensity. This alternative solution is particularly suitable if several luminescent materials, having very different characteristic "decay" time constants, must be analyzed using one and the same equipment.

The method of the present invention relies thus on the use of luminescents which show a time-deferred emission characteristics, and which allows, through a suitable subdivision of the "rise" and "decay" signal observation intervals and the formation of corresponding integrated signal difference values, for an internal compensation of both, ambient background radiation as well as the detector's own back-scattered excitation radiation. This allows for a quantitative assessment even of weak luminescence intensities.

Based on the present teaching, the skilled in the art can easily derive and implement other variants of the disclosed method, in particular such which rely on more than two time intervals for the extraction of luminescence characteristics, and such which rely on observation time intervals of unequal size.

The present invention discloses as well detection equipment which is suitable for the determination of luminescence intensities and other luminescence characteristics, free of contributions from ambient light and from back-scattered excitation radiation. Said equipment relies on the implementation of the method of the invention, in conjunction with at least one luminescent compound showing a time-deferred emission characteristics.

Figure 2B:
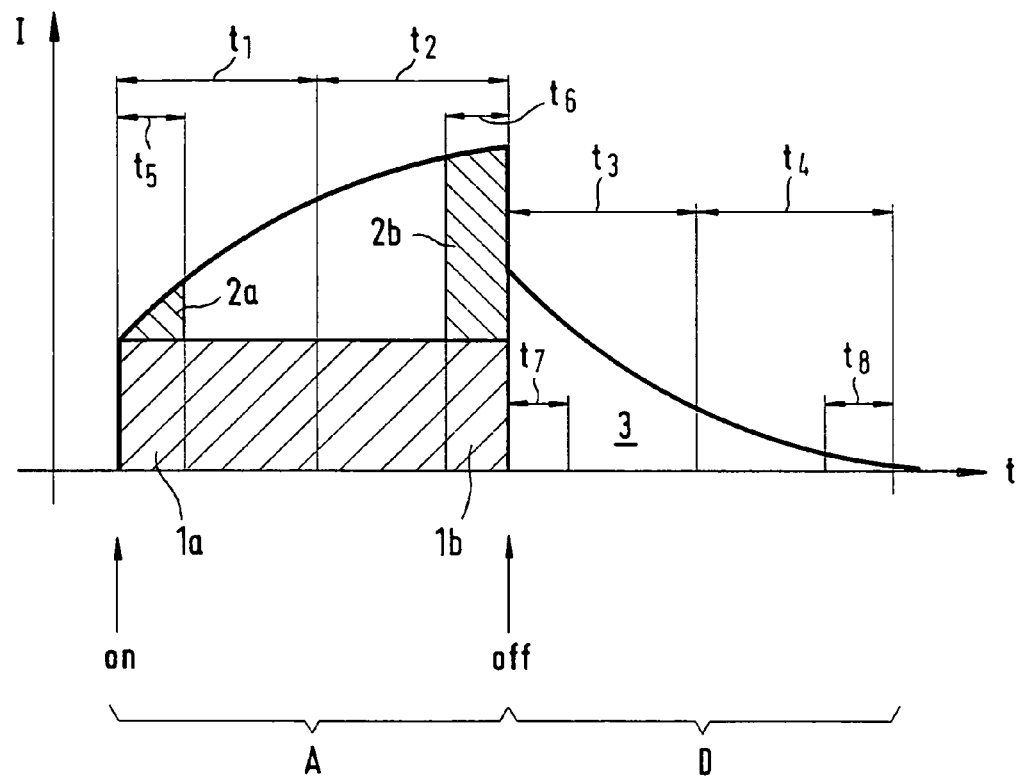

FIG. 2b explains in more detail how the two values of two time intervals, e.g. t5 and t6, may be subtracted from each other: During t5 and t6 the intensity values 1a and 1b which are resulting from back-scattering and other errors are measured. As the time t5 and t6 is equal, the value of 1a and 1b is equal.

The total intensity value during t5 comprises the values 1a and 2a. The total value during t6 comprises 1b and 2b. However, as the intensity value 2a which results from emission of the luminescent material is rather low during the initial phase of illumination, and the value 2b is rather high at the end of the emission cycle, the resulting value of deducting (2b–1b) minus (1a+2a) is very close to the value of 2b. By taking small samples t5 at the beginning of an irradiation cycle and another sample t6 at the end of the irradiation cycle, it is possible to achieve resulting signals, which correspond to a high degree to the intensity of the emitted luminescents. Of course, one could decide to increase the length of one of the sampling periods. If, for example, t6 should be twice as long as t5, exact values will be achieved by dividing the intensity value measured during t6 by the factor 2 to compensate for the longer period of time.

Figure 3:
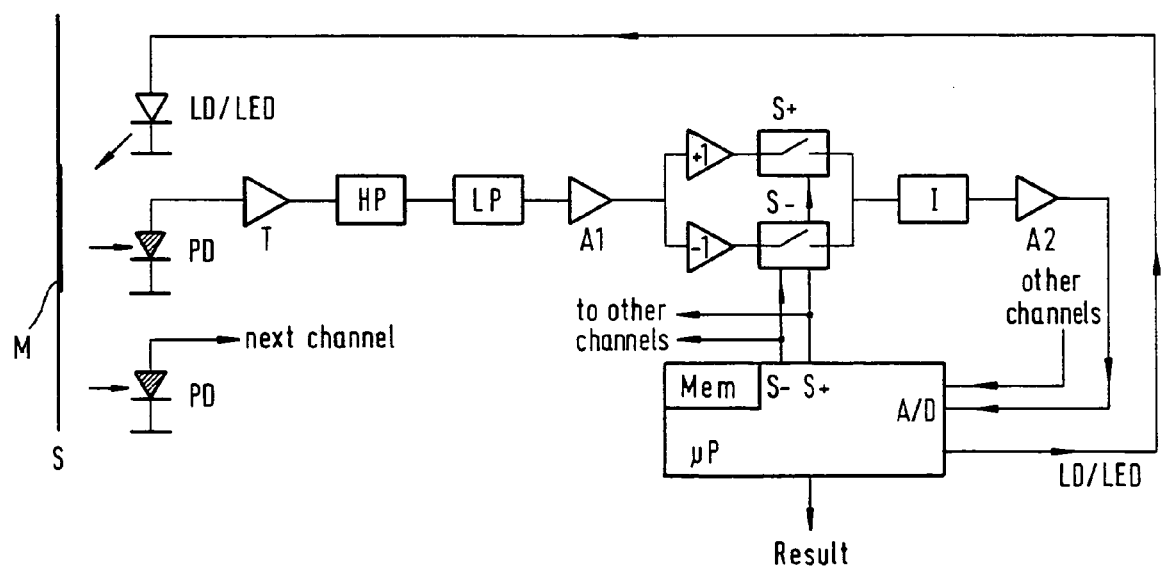

FIG. 3 gives a schematic layout of the functional blocks of said detecting equipment, implementing said method of the invention. Said detection equipment comprises at least one laser-diode or light-emitting-diode as a light light source (LD/LED) for the excitation of a luminescent marking (M) on a sample under test (S). Said detection equipment comprises further at least one microprocessor (μP) with memory (Mem) and at least one analog-to-digital converter (A/D), and at least one detecting channel. Said detecting channel comprises a photodiode (PD), followed by a transimpedance amplifier (T), a high-pass electronic filter (HP), a low-pass electronic filter (LP) and a first signal amplifier (A1). The output of the signal amplifier A1 is fed into a switching unit, comprising a positive branch composed of a non-inverting amplifier of unit gain (+1) and a switching unit (S+), and a negative branch composed of an inverting amplifier of unit gain (−1) and a switching unit (S−). The combined signal of both switching units (S+, S−) is fed into an integrator (I), which is followed by a second signal amplifier (A2). The output of amplifier A2 is finally fed into the A/D converter of the microprocessor (μP).

The detecting equipment comprises at least one, preferably, however, two or more detecting channels, to allow for a relative comparison of luminescence signal intensities originating from a deliberate mixture of different luminescents in a marking. Additional optical or electronic elements may be present in the detecting equipment or in its individual detecting channels, such as focussing or light-collecting lenses, optical filters, electronic filters, etc. Some of the functional blocks indicated in FIG. 3 may also be merged together into a same electronic circuit unit.

Said excitation light source (LD/LED) and said switching units (S+, S−) are controlled by said microprocessor (μP)

and enable the detecting unit to perform arbitrary and application-specific sampling cycles through a corresponding programming of said microprocessor.

The microprocessor (µP) is noteworthy programmed to perform the following operations:

1. repeatedly switch on and off the excitation light source (LD/LED) for determined intervals of time,
2. switch on and off the positive and negative switching units (S+, S−) according to a pre-established sampling scheme,
3. read the detected signal values in digitized form for at least some of the present channels by means of the µP's A/D converter,
4. perform mathematical treatments and absolute or relative comparisons with reference values on the signal values read in step 3,
5. put out the result of step 4 in terms of an authenticity or non-authenticity indication for the sample under test.

Said detecting equipment may furthermore be used either as a stand-alone unit, operating in an autonomous way using pre-stored reference values to determine the authenticity of a sample under test, or, alternatively, in connection a central, secured data server via an information transfer link. Said central server contains the authenticity-reference values and may perform some of the operations of the microprocessor (µP), in particular the ones indicated in steps 4 and 5 above.

The present invention discloses as well a security system, comprising mixtures of luminescent compounds, capable of being identified using said detecting equipment and method. Said mixtures of luminescent compounds may be incorporated in inks and printed onto security documents or articles, or may be molded into plastic or laminated between sheets, for the production of foils, security threads, credit, identity or access cards, and the like. Said security system may noteworthy be employed for protecting banknotes, valued documents, official documents, cards, transportation tickets, as well as branded goods of all kind.

It must also be noted that the method and the equipment according to the present invention allow for a considerable reduction of the optical filtering requirements. If the detection of luminescence response is carried out during the "decay" intervals, where no excitation signal is present, one must not particularly protect the photodiode from the influence of the excitation light. A simple 45° beam-splitter of the rugate-filter type may suffice to isolate the emitted luminescence wavelength. Such filters are advantageous, as they can be mass-produced by Lippmann-holography and related techniques.

In particular cases, one might even envisage to work without any optical filtering, and to rely exclusively on the wavelength discrimination which is already realized through the choice of an appropriate excitation source and an appropriate photodiode, in conjunction with an analysis of the luminescent's decay characteristics, using the method and the device of the invention. In this context it is interesting to note that most LEDs can also be exploited as wavelength-selective, although somewhat less efficient, photodiodes. This is particularly useful when working with up-converting phosphors, in order to reduce the photodetector's sensitivity to the intense longer-wavelength light of the excitation source. As there are plenty of different "colored" LED's on the market, covering the whole spectral range from the near UV, over the visible down into the IR, there are just as many spectrally selective potential photodiodes available to whom would need them.

EXEMPLARY EMBODIMENT

The invention is further illustrated by the drawings and by an exemplary embodiment.

FIG. 1 shows a typical time evolution of the excitation signal and of the detected luminescence response of a luminescent compound used in the present invention: a) intensity versus time of the excitation signal of wavelength $\lambda 1$; b) intensity versus time of the detected response signal. The detected response signal comprises: (1) back-scattered radiation of wavelength $\lambda 1$ leaking through the optical filter system, (2) luminescent radiation of wavelength $\lambda 2$ emitted during excitation, and (3) luminescent radiation of wavelength $\lambda 2$ emitted after excitation.

Figure 4A:
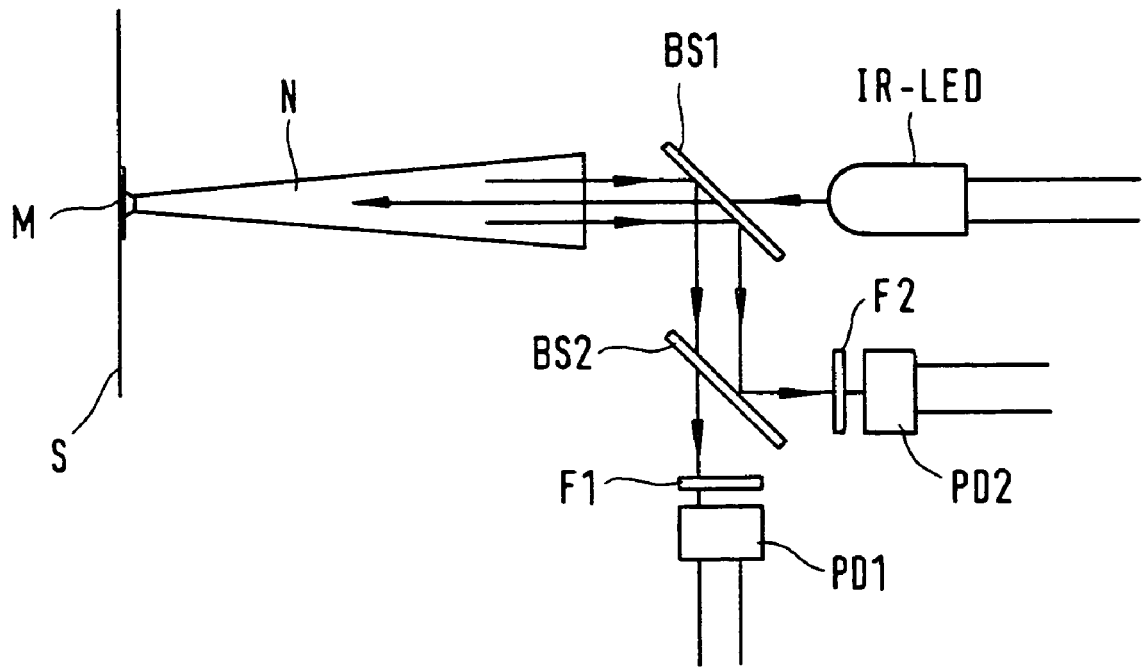
Figure 4B:
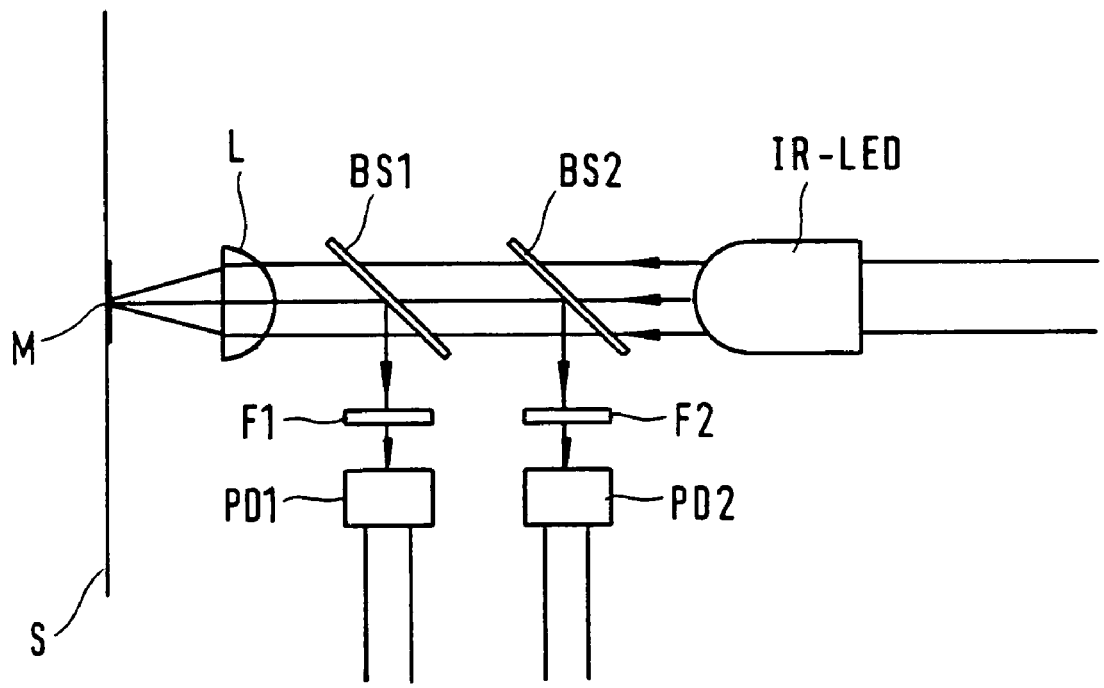
Figure 5:
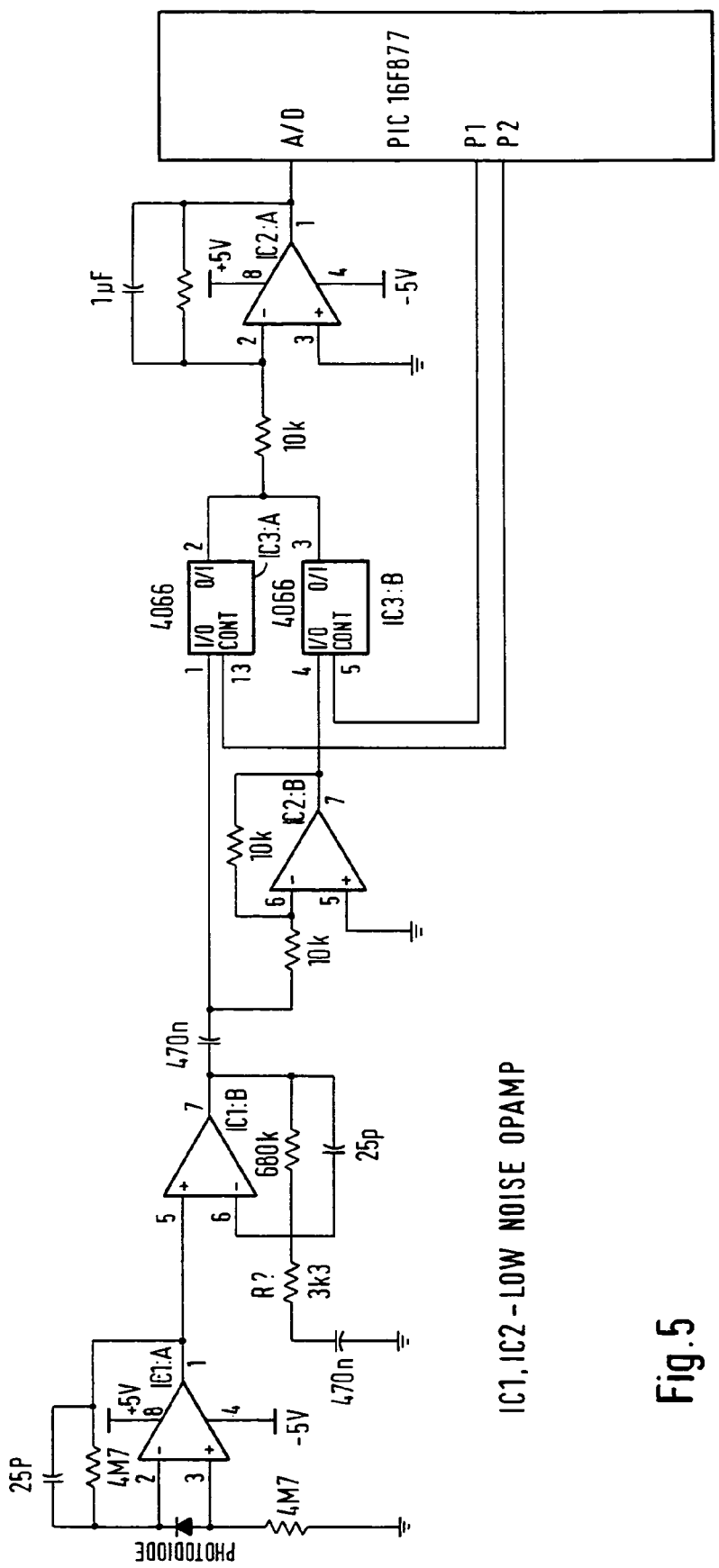

FIG. 2 illustrates the principle of the detection method according to the present invention FIG. 3 shows a block circuit diagram of detecting equipment according to the invention, implementing the method of the invention FIG. 4 shows schematic lay-outs of the optical part of an exemplary embodiment of the invention, comprising an excitation IR-LED and two detection channels: a) a version using non-imaging optics; b) a version using imaging optics FIG. 5 shows the circuit scheme of an electronic embodiment of one detecting channel according to the present invention FIG. 6 example of timing diagrams for the excitation signal (E) and the control signals (P1, P2) of the switching units.

A security system and a corresponding detecting device, implementing the method of the invention were realized as follows. The luminescent compounds were chosen to be up-converting $Y_2O_2S$: Er, Yb and $Y_2O_2S$: Tm, Yb phosphors. Such materials are excitable by intense infrared radiation in the 900 to 980 nm wavelength range. Through a two-photon excitation process, they emit luminescence radiation at shorter wavelength, in the green, 550 nm region for the erbium doped material, and in the near infrared, 800 nm region for the thulium doped material. The characteristic time constants of the corresponding luminescent emission intensity growth and decay are of the order of 50 to 500 µs; they depend noteworthy on the exact nature of the luminescent materials.

The detecting device was constructed according to FIG. 3, FIG. 4 and FIG. 5. The excitation source is a commercially available GaAlAs IR-LED of the type used for remote control applications. The chosen device, OPE5594S, emits an optical power of 120 mW/steradian at a half angle of +/−10°. The peak emission was at 940 nm wavelength, with a spectral half width of 45 nm.

FIG. 4a shows a schematic lay-out of the optical system of the detecting device. The light of said IR-LED is fed via a 45° dielectric beam splitter (BS1) into a conical nozzle (N) of polymethyl-methacrylate (PMMA), and concentrated onto a luminescent marking (M) on the sample under test (S). Said conical nozzle (N) noteworthy acts as a non-imaging optical concentrator (acceptance angle transformer), accepting low-intensity near-parallel-ray light at its wide end and delivering high-intensity, but strongly diverging light at is narrow end. In the opposite sense, it collects a concentrated spot of widely diverging luminescence at its tip and delivers it as a diluted, near parallel beam at its wide end. Beam splitter BS1 is of the long-pass type, having a 45° cut-off wavelength at 900 nm.

The marking (M) contains said two up-converting phosphors in a pre-determined ratio, and emits said two shorter-wavelength luminescent radiation at 550 nm and at 800 nm when excited at high intensity with light of said 900 to 980 nm emitting IR-LED. Said emitted radiation is collected under wide acceptance angle by the conical nozzle (N), "parallelized" and deflected at the first 45° beam splitter BS1. A second 45° dielectric beam splitter (BS2) of the long-pass type, having a 45° cut-off wavelength of 700 nm, separates the 550 nm and the 800 nm components of the emitted luminescence response. The 800 nm component is fed via an optional 800 nm band pass filter (F1) into a silicon photodiode (PD1); the 550 nm component is fed via an optional 500 nm band pass filter (F2) into a GaAsP photodiode (PD2).

An alternative lay-out of the optical system is shown in FIG. 4b. The substantially parallel-beam light of the narrow-angle emitting IR-LED is sent through two dichroitic 45° beam splitters (BS1, BS2) and concentrated by a focussing lens (L) onto a luminescent marking (M) of a sample under test (S). The marking M is hereby disposed in the focal plane of lens L. The luminescence emitted by the marking M in response to the 900 to 980 nm excitation light is collected by lens L and sent back as a parallel-ray light beam onto a first 45° beam splitter (BS1). This beam splitter is of the 45° rugate-filter type and reflects a first narrow wavelength band around 800 nm towards a first photodiode (PD1). The remainder of the light beam falls onto a second 45° beam splitter (BS2). This beam splitter is of the 45° rugate-filter type, too, and reflects a second narrow wavelength band around 550 nm towards a second photodiode (PD2). Optical filters (F1, F2), to cut down the intensity of the back-reflected IR-light of the excitation source, may be optionally inserted in front of the photodiodes (PD1, PD2).

FIG. 5 shows an embodiment of the electronic part of one detection channel of the detecting device. It relies on a microprocessor of the PIC 16F877 type. The microprocessor is common to all detection channels of the detecting device. The detector electronics relies on inexpensive electronic components; i.e. the low-noise operational amplifiers may be of the NE 5532 type (2 units per casing), and the switching units may be of the 4066 type (4 units per casing).

The photodiode, which may be of the silicon, GaAsP, or any other type, is exploited in photovoltaic mode and delivers its signal to a balanced transimpedance amplifier stage (IC1:A). Said transimpedance amplifier stage is followed by a second amplifier stage (IC1:B), which delivers its output, through capacitance coupling, to the positive and the negative switching units (IC3:A, IC3:B). For the positive unit (IC3:A), the output signal of IC1:B is directly used; for the negative unit (IC3:B), the output signal of IC1:B is first fed through an analog-inverter stage (IC2:B). The combined output of the switching units (IC3:A, IC3:B) is fed into an integrator stage (IC2:A) and the integrated signal goes to the analog-to-digital converter (A/D) of the PIC processor. The control signals (P1, P2) for the switching units (IC3:A, IC3:B) are generated by the PIC processor.

Based on the foregoing teaching, it is easy for the skilled in the art to conceive further embodiments of the detecting device which, in particular, may have more than one excitation light source, or more than two detecting channels.

The operation frequency of the device of our exemplary embodiment was chosen to be 1 kHz, with equal lengths of the excitation-on and the excitation-off time intervals. This is, however, not a necessary condition; one may equally chose other on/off ratios.

FIG. 6 illustrates an example of useful timing diagrams for the excitation signal (E) and the control signals (P1, P2) of the switching units. FIG. 6a shows the square-wave excitation signal (E) and the luminescence response (R). FIG. 6b shows an example of sampling the "rising" part of the luminescence response (R) using the switching units' control signals (P1, P2). FIG. 6c shows an example of sampling the "decay" part of the luminescence response (R). FIG. 6d shows an alternative example of sampling the "rising" part of the luminescence response (R).

The method and the device of the invention allow noteworthy, through a combination of suitable different sampling schemes, to extract information about both, the luminescence intensity and the characteristic time constants of the "rise" and the "decay" part of the luminescence response (R).

The invention claimed is:

1. A method for authenticating a security marking comprising a luminescent compound by exposing the marking to an excitation, said luminescent compound being excitable by an excitation light source, and measuring the intensity of the luminescence emission wherein during or after exposure to the excitation light source light-intensity values are measured during specific intervals of time which are selected that, after subtracting the intensity value collected during one time interval from the intensity value collected during another time interval, the result of the subtraction is representative for light emitted from the luminescent compound, wherein the duration of one time interval is shorter than 25% of the duration of the exposure of the luminescent compound to the excitation light source.

2. A method according to claim 1, wherein one of the time intervals is selected during the initial phase of the excitation of the luminescent compound to reduce the proportion of light intensity resulting from emission of the luminescent compound compared to measured light intensity caused by light, stray light which does not result from emission.

3. A method according to claim 1, wherein another one of the time intervals is selected during a phase in which the intensity of luminescent emission has risen to its maximum.

4. A method according to claim 1, wherein the marking comprises one or more luminescent compounds, said luminescent compounds emitting light at two different frequencies and intensity values are sampled for light emitted at said frequencies.

5. A method according to claim 4, wherein the intensity values of said different frequencies are compared.

6. A method according to claim 1, wherein light intensity is sampled during exposure of the marking to irradiation.

7. A method according to claim 1, wherein light intensity is sampled after exposure of the marking to irradiation.

8. A method according to claim 1, wherein the light intensity values during the time periods are integrated.

9. An authentication device comprising
a light emitting device for exciting a luminescent marking,
a device for measuring intensity of light emitted by the marking during at least two time intervals,
a device for subtracting values of the emitted light intensity and for generating output signals for performing the method according to claim 1.

10. An authentication device according to claim 9, further comprising a device for measuring emitted light intensity over two or more frequency ranges of the light.

11. A system comprising
an authentication device according to claim 9 and
a composition for creating a security marking comprising
a luminescent compound, said luminescent compound being capable of being detected by said authentication device.

12. A method for marking and authenticating security documents or articles, said method relying on the use of at least one luminescent compound, said luminescent compound being excitable by an excitation light source and showing a build-up in time of the luminescence emission intensity after the excitation light source has been switched on, and a decay in time of the luminescence emission intensity after the excitation light source has been switched off, wherein
- said luminescent compound is part of a security document or article, and said method comprises steps of
- switching said excitation light source on during a first time interval and off during a second time interval,
- measuring at least two luminescence intensity values for at least one luminescence wavelength at least during two subsequent third and fourth time intervals inside either first time interval or second time interval or both, wherein the duration of one of said third and fourth time intervals is shorter than 25% of the duration of the exposure of the luminescent compound to the excitation light source, and
- subtracting at least one of said measured luminescence intensity values from another such value to obtain net luminescence intensity values, and
- comparing said net luminescent intensity values to reference values, as an authenticity criterion.

13. A method according to claim 12, wherein said third and fourth time intervals are equal and lie within said first time interval.

14. A method according to claim 12, wherein said third and fourth time intervals are equal and lie within said second time interval.

15. A method according to claim 14, wherein said third and fourth time intervals are each half of said second time interval.

16. A method according to claim 12, wherein said excitation light source is repeatedly switched on and off, and wherein said luminescent intensity values are repeatedly measured and subtracted, to obtain integrated net intensity values, which are compared to reference values, as an authenticity criterion.

17. A device for authenticating security documents or articles, said documents or articles carrying at least one luminescent compound, said luminescent compound being excitable by an excitation light source and showing a build-up in time of the luminescent emission intensity after the excitation light source has been switched on, and a decay in time of the luminescent emission intensity after the excitation light source has been switched off, said device comprising
- at least one excitation light source, at least one photodetector channel, and at least one microprocessor, wherein
- said excitation light source is capable of being switched on during a first time interval and of being switched off during a second time interval under control of said microprocessor,
- said photodetector channel comprises at least one photodetector, producing an analog output signal when illuminated by a light source, and at least one signal sampling unit, capable of sampling and integrating, under control of said micro-processor, non-inverted and inverted portions, respectively, of said photodetector output signal during third and fourth time intervals, wherein the duration of one of said third and fourth time intervals is shorter than 25% of the duration of the exposure of the luminescent compound to the excitation light source, producing at least one net output signal, and
- said microprocessor is capable of digitizing and storing said at least one net output signal.

18. A device according to claim 17, wherein said third and fourth time intervals are equal and lie within said first time interval.

19. A device according to claim 17, wherein said third and fourth time intervals are equal and lie within said second time interval.

20. A device according to claim 19, wherein said third and fourth time intervals are each half of said second time interval.

21. A device according to claim 17, wherein said excitation light source is repeatedly switched on and off, and said signal sampling unit repeatedly samples and integrates said photodetector output signal, obtaining at least one integrated net output signal.

22. A device according to claim 21, wherein said at least one integrated net output signal is locally compared by said microprocessor with at least one internally stored reference value, to derive an authenticity signal.

23. A device according to claim 21, wherein said at least one integrated net output signal is transmitted via a communication link to a remote server, to be compared with at least one stored reference value, to derive and send back an authenticity signal.

24. A device according to claim 17, wherein said at least one net output signal is locally compared by said microprocessor with at least one internally stored reference value, to derive an authenticity signal.

25. A device according to claim 17, wherein said at least one net output signal is transmitted via a communication link to a remote server, to be compared with at least one stored reference value, to derive and send back an authenticity signal.

26. A security system comprising
- plural luminescent markers having time-deferred emission characteristics, said
- plural luminescent markers being incorporated at different ratios in inks or plastic materials for the production of security documents or articles, and
- a device according to claim 17, for determining the authenticity of said security documents or articles.

27. A security system according to claim 26, wherein said luminescent markers have different emission wavelengths.

28. A security system according to claim 26, wherein said device comprises a corresponding number of detecting channels.

* * * * *

UNITED STATES PATENT AND TRADEMARK OFFICE
CERTIFICATE OF CORRECTION

| | | |
|---|---|---|
| PATENT NO. | : 7,030,371 B2 | Page 1 of 1 |
| APPLICATION NO. | : 10/240737 | |
| DATED | : April 18, 2006 | |
| INVENTOR(S) | : Vasic et al. | |

It is certified that error appears in the above-identified patent and that said Letters Patent is hereby corrected as shown below:

On Title page, Item [75], Col. 1, in the Inventor information, change the citizenship of the third inventor Myron Seto from "(CH)" to -- (US) --

On Title page, Col. 1 after Prior Publication Data, insert the following:

-- (30)  Foreign Application Priority Data
March 1, 2001 (EP)……………………………..01105020.0 --

Signed and Sealed this

Fourth Day of July, 2006

JON W. DUDAS
*Director of the United States Patent and Trademark Office*